United States Patent

Jansson et al.

[11] Patent Number: 5,345,929
[45] Date of Patent: Sep. 13, 1994

[54] PUMPING DEVICE

[76] Inventors: Lars-Erik Jansson, Vretvágen 4A, 80426 Gávle; Hans-Ake Stööp, Rotvaltan 19, 80431 Gávle; Sven E. U. Stattin, Alpgatan 38, 35241 Váxjó, all of Sweden

[21] Appl. No.: 960,462
[22] PCT Filed: Jun. 11, 1991
[86] PCT No.: PCT/SE91/00417
    § 371 Date: Dec. 15, 1992
    § 102(e) Date: Dec. 15, 1992
[87] PCT Pub. No.: WO91/19525
    PCT Pub. Date: Dec. 26, 1991

[30] Foreign Application Priority Data
Jun. 11, 1990 [SE] Sweden .................. 9002073

[51] Int. Cl.⁵ ............................ A62B 7/00
[52] U.S. Cl. .................. 128/205.13; 128/205.14; 128/206.27
[58] Field of Search ........... 128/205.13, 205.14, 128/205.15, 205.16, 206.27

[56] References Cited

U.S. PATENT DOCUMENTS

| | | | |
|---|---|---|---|
| 1,157,655 | 10/1915 | Mayer et al. | 128/205.18 |
| 1,197,232 | 9/1916 | Pierport | 128/205.13 |
| 1,202,125 | 10/1916 | Tullar | 128/205.13 |
| 1,371,702 | 3/1921 | Lyon | 128/205.18 |
| 2,364,626 | 12/1944 | Emerson | 128/204.25 |
| 2,428,451 | 10/1947 | Emerson | 128/205.13 |
| 3,058,460 | 10/1962 | Goodner | 128/205.13 |
| 3,316,903 | 5/1967 | Richards | 128/205.16 |
| 3,461,865 | 8/1969 | Chouinard et al. | 128/205.24 |
| 3,818,806 | 6/1974 | Fumagalli | 128/205.13 |
| 3,939,830 | 2/1976 | da Costa | 128/205.18 |
| 4,060,077 | 11/1977 | Friedman | 128/205.16 |
| 4,187,845 | 2/1980 | Dror | 128/205.13 |
| 4,349,015 | 9/1982 | Alferness | 128/205.16 |
| 4,870,962 | 10/1989 | Sitnik | 128/205.13 |
| 4,898,166 | 2/1990 | Rose et al. | 128/205.13 |
| 4,898,167 | 2/1990 | Pierce et al. | 128/205.16 |

FOREIGN PATENT DOCUMENTS

| | | |
|---|---|---|
| 114368 | 6/1969 | Denmark . |
| 1491776 | 7/1965 | Fed. Rep. of Germany . |
| 202763 | 10/1958 | Sweden . |
| 207473 | 10/1962 | Sweden . |
| 204460 | 11/1963 | Sweden . |

OTHER PUBLICATIONS

U.S. Armed Forces Medical Journal A61M16/00P-,M—Jun., 1956.

Primary Examiner—Edgar S. Burr
Assistant Examiner—Aaron J. Lewis
Attorney, Agent, or Firm—Zarley, McKee, Thomte, Voorhees & Sease

[57] ABSTRACT

A pumping apparatus of the bellows type, which is adapted for artificial respiration of a distressed person having temporarily no ability to breathe by himself, comprises a bag (2), arranged with two mutually movable walls (3,4) delimiting the inner volume thereof, to participate in delimiting the inner volume of the bellows (5). The ends of the folded bellows wall are fastened to one of the two walls each and the pump is arranged to force the air contained in the bellows space aside and to suck air thereinto by movement of the two walls (3,4) towards each other and away from each other, respectively.

6 Claims, 3 Drawing Sheets

PUMPING DEVICE

The present invention relates to a pumping apparatus of the bellows type, which is adapted for artificial respiration of a distressed person having temporarily no ability to breathe by himself.

The reason for using pumps for carrying out an artificial respiration is that the rescuing person otherwise may run the risk of fainting as a consequence of hyperventilation. Furthermore, it is difficult to blow in a well balanced amount of air using the mouth-to-mouth-method. In addition thereto it may often be uncomfortable to carry out the mouth-to-mouth-method with the distressed person, since this may be influenced by drugs or in another way acting repellently. The fear for transmission of deceases, such as AIDS, may also contribute to this.

A series of pumps for breathing aid are already known, and the one according to U.S. Pat. No. 2,364,626 may be mentioned. A disadvantage of these pumps already known is that they are constructed unnecessarily complicatedly and by that costly to manufacture, and they are also inconvenient to carry along, not least for the reason that they require a comparatively big storing space.

A pumping apparatus according to the type mentioned in the introduction is already known through U.S. Pat. No. 2,428,451. Owing to the fact that the pump is of the bellows type, it is possible to reduce the demand on space thereof in the unused storing position, but some kind of device for holding the bellows together would be necessary for achieving this. Furthermore, the pumping apparatus according to the patent last mentioned is comparatively complicatedly constructed and inconvenient to carry along.

BRIEF DESCRIPTION OF THE INVENTION

The object of the present invention is to provide a pumping apparatus of the kind defined in the introduction, which remedies the inconveniences of pumping apparatuses already known.

In accordance with the invention this object is obtained by providing such a pumping apparatus with the characteristics defined in the characterising part of the appended claim 1.

By the fact that the pumping apparatus according to the invention comprises a bag with two mutually movable walls, that the ends of the folded bellows wall are fastened to one of the two walls each and that the pump is arranged to force the air contained in the bellows space aside and to suck air thereinto by movement of the two walls towards each other and away from each other, respectively, a very simply constructed pumping apparatus is obtained, which also may be stored and carried along in a very compact state. Accordingly, this is enabled through the fact that a bag or a case functions as a part of the pump itself and also may contain the bellows. The other parts included in the pumping apparatus may also be contained in the bag in its storing state if the bag of the pumping apparatus according to the invention is suitably dimensioned. This means that the pumping apparatus becomes very easy to carry along and the risks of damaging the parts included therein during transport will also be a minimum, since the walls of the bag will function as a protection thereof.

Further advantages and preferred characteristics of the invention will appear from the following description as well as the appended dependent claims.

BRIEF DESCRIPTION OF THE DRAWINGS

With reference to the appended drawings, below follows a specific description of a preferred embodiment of the present invention cited as an example.

In the drawings.

DETAILED DESCRIPTION OF A PREFERRED EMBODIMENT OF THE INVENTION

Figure 1:
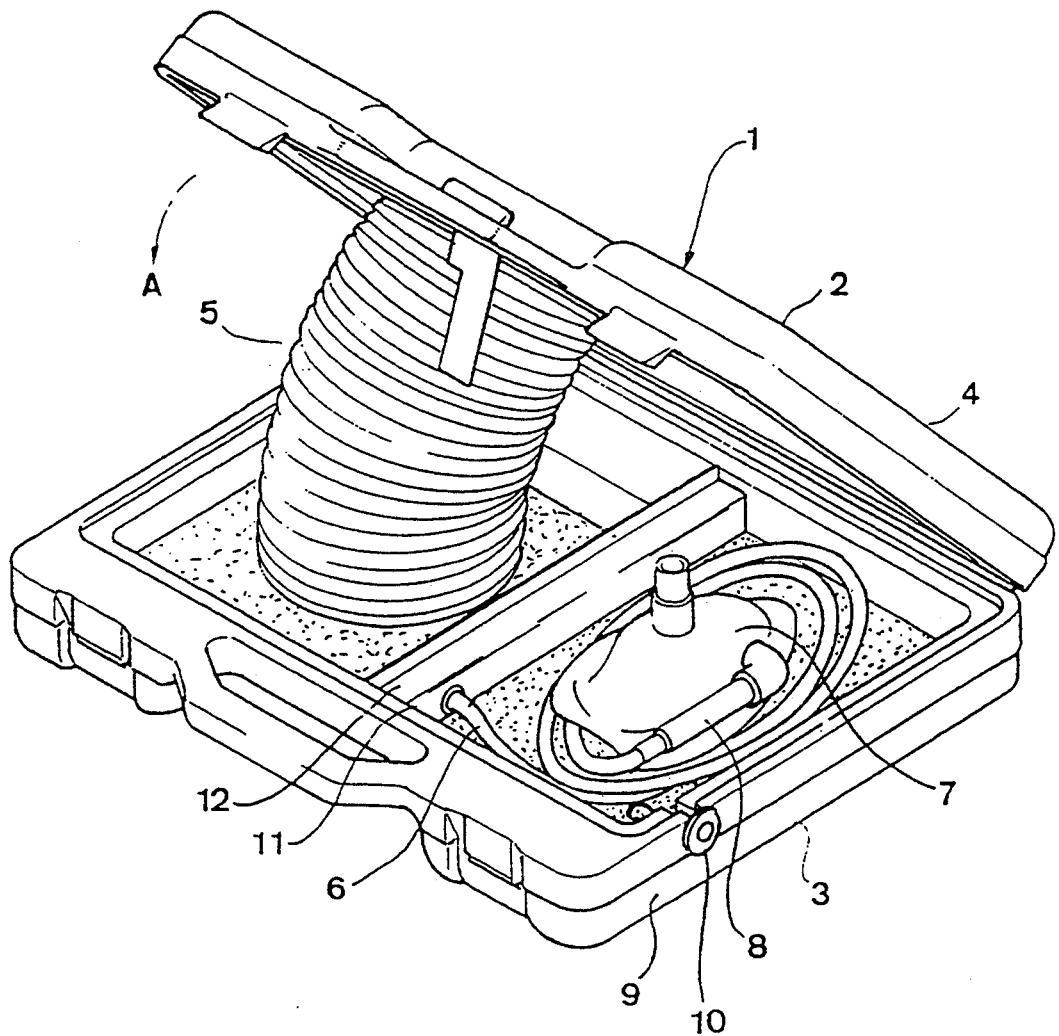
FIG. 1 is a perspective view of the pumping apparatus according to the invention just opened after transport.

A preferred embodiment of the pumping apparatus 1 according to the invention is shown in FIG. 1, said apparatus comprising a bag or case 2 with a bottom member 3 and a lid 4 pivotally connected thereto. A conventional bellows 5 is arranged between the bottom member 3 and the lid 4, so that parts of the bottom member and the lid delimit a pump volume together with the folded bellows wall. A hose 6 is connected to the interior of the bellows. The bellows 5 is compressed and air contained therein is pressed out through the hose 6 by pivoting the lid 4 from the position shown in FIG. 1 in the direction of the arrow A towards the bottom member 3. The bellows 5 is provided with a suitable valve, for instance a plate setting the opening of the hose in the bellows free on said compression, said valve closing the hose opening and opening an opening (not shown) located between the bottom member and the bellows for letting air flow into the bellows when the lid 4 is pivoted back in the direction opposite the arrow A. The last mentioned opening is intended to be obstructed by said valve on the movement in the direction of the arrow A, so that the air contained in the interior of the bellows 5 only can escape through the hose 6. Thus, the bag 2 with the bottom member 3 and the lid 4 functions together with the bellows 5 as a conventional pump of the bellows type.

A face mask 7 for connecting the hose 6 to the breathing paths of a person normally distressed is also arranged inside the bag 2. The hose 6 is terminated by a stiff tube 8, which contains a valve device to be explained furtheron. An opening closable by a plug 10 is arranged in one side wall 9 of the bottom member 3 so as to permit the hose 6 to be past to the exterior after removing the plug 10, so that the lid 4 may be brought completely together with the bottom member 3 without the hose 6 being jammed (see FIG. 2) on using the bag as a pump. A rail 11 with a support and slide surface 12 directed substantially parallelly to the bottom of the bottom member is also arranged in the interior of the bag 2. The task of this rail will be explained furtheron with reference to FIGS. 3 and 4.

Figure 2:
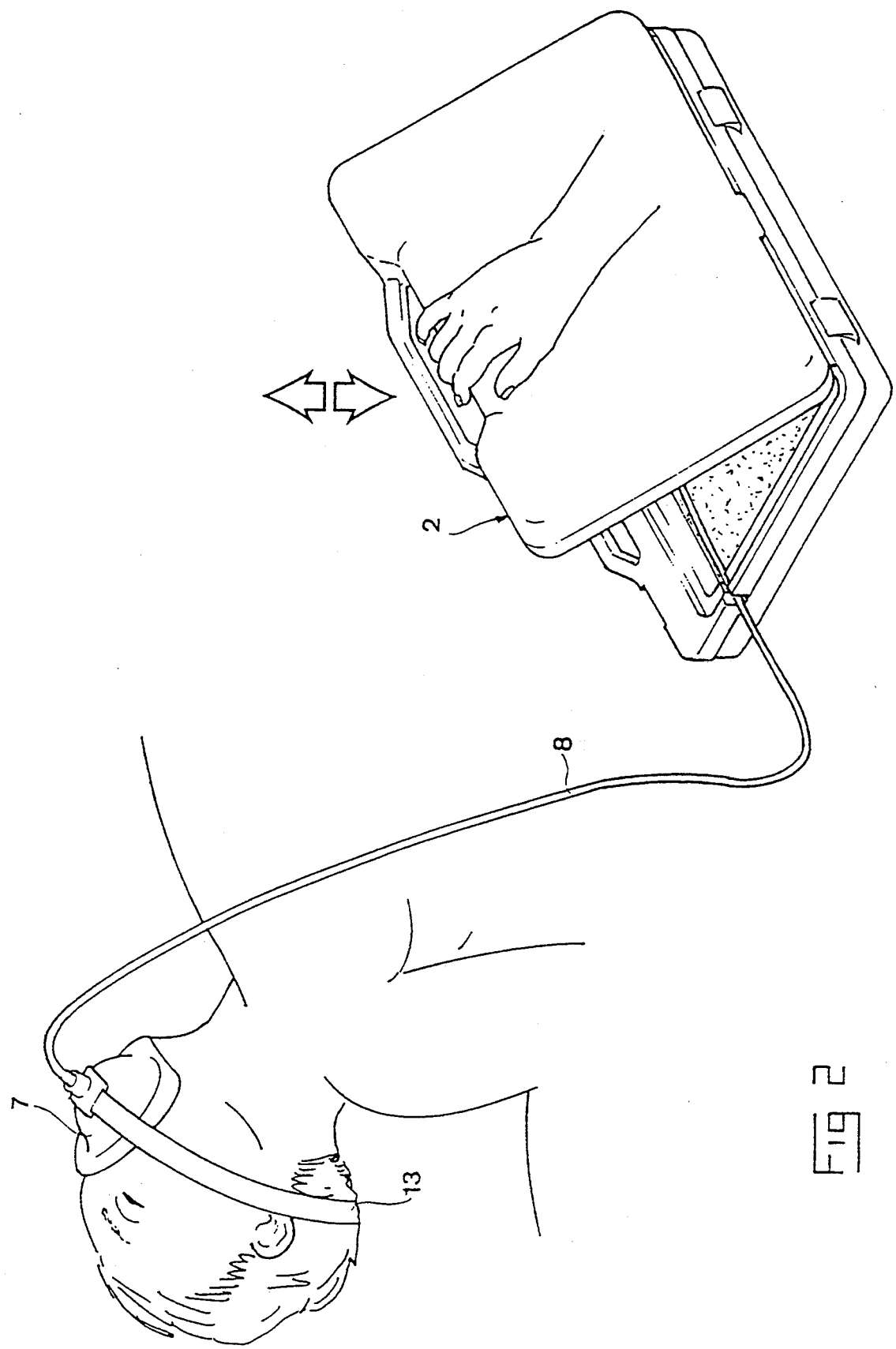
FIG. 2 is a schematic view illustrating the use of the apparatus according to FIG. 1, FIG. 3 and 4 are side elevations of the apparatus according to FIG. 1 with parts of the bag walls broken away so as to illustrate a bar for protection against-pumping of great amounts of air into the lungs of small persons, such as children.

In FIG. 2 it is schematically shown how the pumping apparatus according to the invention may be used in assisting a distressed person to breathe. The pumping apparatus according to the invention may easily with a low space demand be carried along by for instance ambulance staff and police officers. It may also be arranged in vehicles for transporting greater amounts of people, such as busses and trains. It would also be conceivable that sport arenas, entertainment parks and the like are provided with a pumping apparatus according to the invention for use when accidents happen in connection with bigger events. Swimming areas have also a need of an apparatus according to the invention. When a user of the pumping apparatus with the bag 2 arrives to a distressed person, the bag is opened and laid on the bottom member thereof. After that a plug 10 is removed, the stiff tube 8 is connected to the face mask 7, the hose 6 is passed through the opening set free by the plug 10 and the face mask 7 is applied over the breathing paths of the distressed person and held by a strap 13 in place. Pumping air into the lungs of the distressed person may thereafter begin. Thus, the bag easy to carry along may in a very short period of time be transformed into a breathing apparatus for life-saving.

Figure 3:
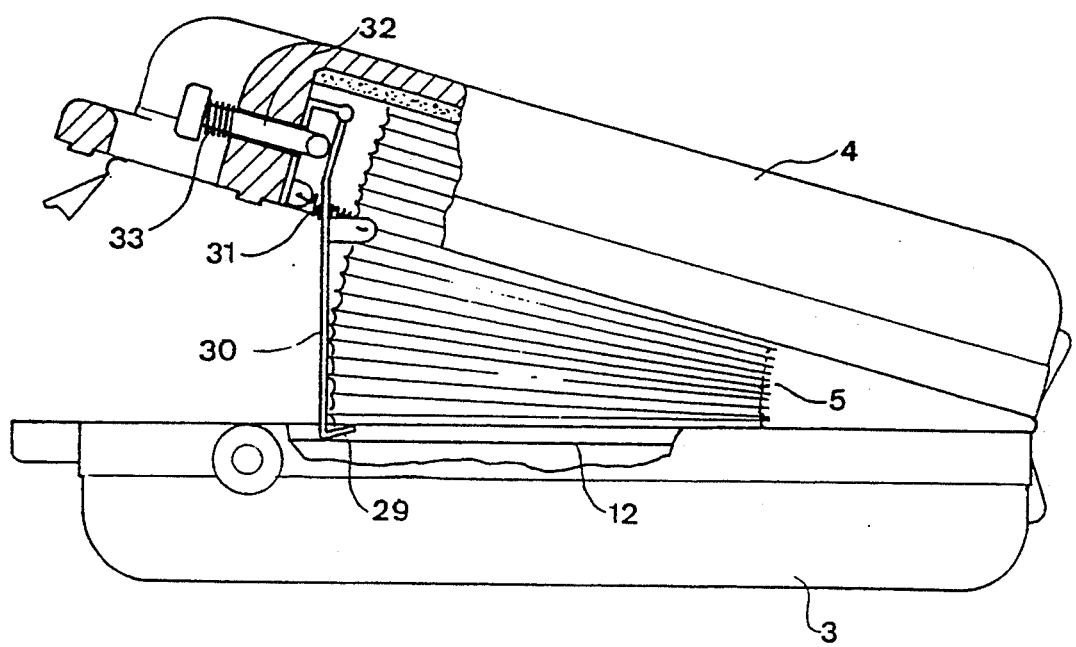
Figure 4:
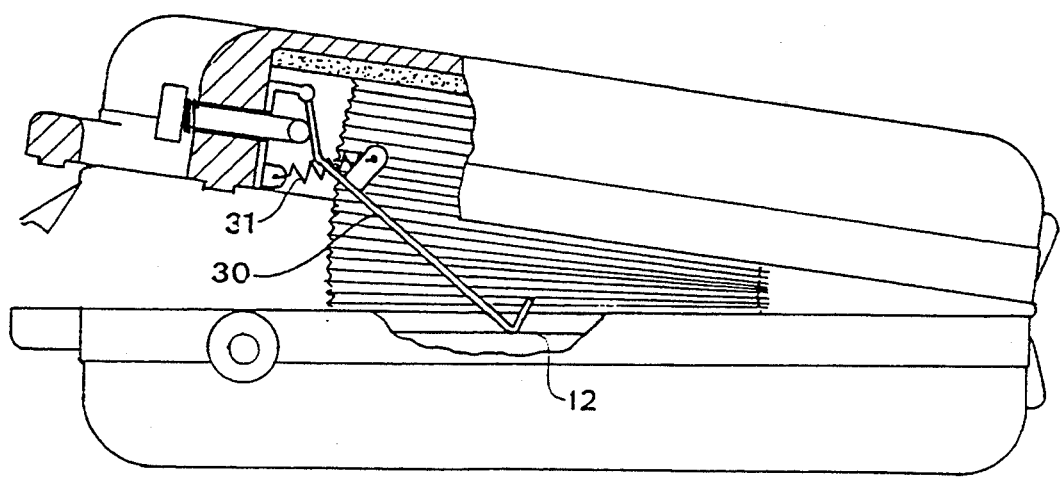

A member for adapting the gas volume which may maximally be forced aside per pumping stroke of the apparatus according to FIG. 1 to the lung size of a distressed person will now be explained with reference to FIG. 3 and 4. A sheet-like projection 30 terminated by an angle piece 29 is pivotally suspended in the lid 4 of the bag about an axis being substantially parallel to the pivot axis for the connection of the lid 4 with the bottom member 3. The projection 30 may be pivoted counter-clockwise as seen in FIG. 3 with the angle piece 29 inwardly towards the lid 4 against the action of a tension spring 31. The projection 30 may not pivot any longer in the opposite direction then to the position shown in FIG. 3, in which it hits a pin-like pressing member 32. This pressing member 32 may be pressed inwardly (see FIG. 4) while compressing and storing potential energy in a compression spring 33, by which one of the end positions of the projection 30 is displaced counter-clockwise. The pressing member 32 is intended to be influenced by the hand of a person and returns automatically to the position according to FIG. 3 when such influence is stopped.

The protection bar just explained function in the following way: when operating the pumping apparatus without any influence upon the pressing member 32, when the angle piece 29 reaches the position shown in FIG. 3 the projection 30 will upon attempts to further compress the bellows 5 be influenced by reaction forces on the angle piece 29 emanating from the surface 12 of the rail 11 to pivot clockwise. However, such pivoting is made impossible by the pressing member 32, which means that the position shown in FIG. 3 is a position for maximum compression of the bellows 5 at not influenced or actuated pressing member 32. Thus, using the pumping apparatus without influencing the pressing member means that a reduced volume of air may be pumped per pump stroke, which is suitable for the use of the apparatus on persons with small lungs, primarily children. On the other hand, if the apparatus is to be used on an adult the pressing member 32 is kept pressed in on carrying out the pumping, which means that the projection 30 with the angle piece 29 hits the guide and slide surface 12 of the rail 11 with such an angle that the reaction forces from the latter tend to pivot the projection 30 counter-clockwise as seen in FIG. 4 on extension of the tension spring 31. Thus, when the lid 4 continues to get closer to the bottom member 3 the projection 30 slides by means of the angle piece 29 on the guide and slide surface 12 while the projection 30 is pivoted towards the lid, so that the lid and the bottom member may be pressed together. The pumping apparatus may by that be brought to pump a maximum amount of air per pump stroke, which is suitable for an adult. However, a refused amount of air, preferably half as much as the maximum amount of air, is always pumped in the uninfluenced position, which ensure that one will not accidentally pump to much air into the lungs of a little child, which would lead to a catastrophe.

The invention is of course not in any way restricted to the preferred embodiment described above, but several possibilities to modify it would be apparent to a man skilled in the art without departing from the basic idea of the invention.

The bag may for instance have another outer shape than shown in the figures.

Furthermore, the face mask may be differently designed.

It would of course also be possible to omit the child protection bar and have one single possible pump volume, so that there could be special bags for children and adults, but this would of course hardly be just as suitable as a bag for both big and small people.

The lid of the bag could of course be located undermost and the bottom member be pivoted with respect thereto during the pumping, but also other orientations of the bag would be conceivable, such as for instance with the opening directed upwardly.

A filter for catching air contaminations could be arranged in the bellows, the hose or in connection to the face mask.

We claim:

1. A pumping apparatus of the bellows type, which is adapted for artificial respiration of a distressed person temporarily unable to breathe on their own, comprising:

a substantially rigid dual-purpose pumping/carrying case having a bottom and a lid pivotally connected to said bottom so as to define a carrying space between said lid and said bottom;

a bellows housed substantially within said case having a folded wall enclosing a bellows space and having two ends; one of said ends being fastened to said lid and the other of said ends being fastened to said bottom so as to establish a variable volume within said bellows space;

whereby said bellows space is expanded to draw air thereinto by pivoting said lid and said bottom away from each other in the direction of opening said case and said bellows space is compressed to force air contained therein out by pivoting said lid and said bottom toward each other in the direction of closing the case; and said carrying space of said case being substantially greater in volume than said bellows space when the latter is fully compressed and said case is closed, such that useful carrying space remains available for carrying items in said case in addition to said bellows.

2. A pumping apparatus according to claim 1 wherein said case has an elongated air outlet conduit having two ends, one end connected to said bellows space and another end connected to means for connecting said conduit to the breathing paths of a distressed person.

3. A pumping apparatus according to claim 1 wherein said apparatus is a hand pump having a means for selectively limiting the stroke of compression of said bellows, said means having a free state in which the compression stroke is limited and a manually activated state in which the maximum compression stroke is allowed.

4. A pumping apparatus according to claim 3, characterized in that said member comprises a projection pivotally connected to said lid about an axis being substantially parallel to the pivot axis of said lid, said projection being directed substantially towards said bottom in said free state, that the projection may be folded back towards said lid in the one pivoting direction and arranged to hit a stop on trying to pivot in the opposite pivoting direction, and that the projection is arranged to, when said lid and bottom are pivoted towards each other in said free state, hit said bottom or a piece connected thereto and by this be influenced towards said stop and prevent further getting closer of said lid and bottom and in a said manually activated state through an operating member connected thereto, by the fact that the operating member is arranged to change the direction of the projection with respect to said bottom, hit said bottom or said piece connected thereto while generating forces folding the projection back towards said lid when trying to bring said lid and bottom even closer to each other.

5. A pumping apparatus according to claim 4, characterized in that said bottom is adapted to be placed on a substantially horizontal ground when the pump is used, that the pivot axis of the projection is directed substantially horizontally then, that a spring member is arranged to prevent the projection from pivoting more than to a position leading to pivoting of the projection in the direction towards the stop as a consequence of the gravitation acting thereupon when the projection is hitting said bottom or said piece connected thereto, and that the operating member has a pressing member arranged to pivot the projection on action upon the operating member while accumulating energy in the spring member, to a position leading to a folding back of the projection while sliding with its outer end on a slide surface arranged on said bottom when it hits said bottom or said piece connected thereto.

6. The apparatus of claim 1 wherein the case is a briefcase having a handle attached to said bottom for carrying said case.

* * * * *